United States Patent [19]

Ewbank

[11] 3,971,842

[45] July 27, 1976

[54] CONTINUOUS DISPLACEMENT CHROMATOGRAPHIC SEPARATION

[75] Inventor: John R. Ewbank, Southampton, Pa.

[73] Assignee: Atlantic Richfield Company, Los Angeles, Calif.

[22] Filed: Aug. 8, 1974

[21] Appl. No.: 495,695

[52] U.S. Cl. .................................. 423/7; 210/267; 423/8
[51] Int. Cl.² .................. C22B 60/02; B01D 15/08; B01D 33/00
[58] Field of Search ..................... 423/7, 8; 210/267

[56] References Cited
UNITED STATES PATENTS

| | | | |
|---|---|---|---|
| 3,511,620 | 5/1970 | Shimokawa | 423/7 |
| 3,869,536 | 3/1975 | James | 423/7 |

FOREIGN PATENTS OR APPLICATIONS

| | | | |
|---|---|---|---|
| 871,539 | 6/1961 | United Kingdom | 423/8 |

OTHER PUBLICATIONS

Swinton et al., Australian Journal of Applied Science, vol. 4, No. 2, June, 1953, pp. 316–328.

Primary Examiner—Leland A. Sebastian
Assistant Examiner—Christine M. Nucker
Attorney, Agent, or Firm—John R. Ewbank

[57] ABSTRACT

In a plant for uranium enrichment using a cascade of ion exchange beds, each bed operates more efficiently because an annular chamber is rotated about a stationary annular ion exchange bed at a speed corresponding to the speed of migration of a region so that, with respect to such rotating chamber, each of the regions of a system remains substantially stationary. An aqueous solution of ferric chloride is pumped to the ferric region and flows forwardly to the forwardly moving rear boundary of the uranium region.

7 Claims, 10 Drawing Figures

CONTINUOUS DISPLACEMENT CHROMATOGRAPHIC SEPARATION

FIELD OF THE INVENTION

This invention concerns the displacement-chromatographic separation of a mixture of ions by ion exchange. The subject matter concerns chromatographic displacement of a separation region along the length of an elongated ion exchange bed by boundary reactions comprising displacement of the separating mixture at one boundary of a principal chromatographic separation region and resorption of that mixture at the other boundary. One embodiment contemplates upgrading uranium to contain sufficient $U^{235}$ isotope for use as fuel in a nuclear reactor.

PRIOR ART

There are several difficult chemical or isotopic separations problems which have been solved by the application of displacement-chromatographic ion-exchange processes. However, these separations have always been effected using fixed beds or columns of ion-exchange material through which a fluid phase, usually aqueous and containing the species to be separated, is percolated. Previous attempts to apply continuous ion-exchange contactors, where the resin phase also moves, to these separations problems have not been wholly successful, usually due to the loss of stage efficiency because of back mixing. Some of the difficult chemical or isotopic separations problems that have been solved by fixed-bed displacement-chromatographic ion exchange include the separation of zirconium from hafnium; the separation of neighboring pairs of the lanthanide and actinide elements; and the separation of the hydrogen, boron, nitrogen, and uranium isotopes. The general applicability of the present invention to these separations problems will be recongnized by considering several of them in detail.

It is of great importance to separate the isotopes of boron because $^{10}B$ has a thermal-neutron cross-section of 3840 barns and a relative natural abundance of about 20 per cent, while $^{11}B$ has a thermalneutron cross-section of only 0.0005 barns and a relative natural abundance of about 80 per cent. Therefore, the value of boron as a thermal-neutron control or burnable poison in nuclear power reactors is greatly enhanced by removing the $^{11}B$ from the naturally occurring isotopic mixture.

When an aqueous solution of boric acid, $HBO_2$, encounters an anion-exchange bed containing the borate ion, $BO_2^-$, the anion-exchange equilibrium tends to favor the enrichment of the $^{10}B$ isotope in the borate ions on the anion-exchange bed and to favor the proportional concentration of the $^{11}B$ isotope in the boric acid solution. A displacement chromatographic technique with fixed-bed anion-exchange columns for multiple repetition of this equilibration to achieve satisfactory separation of the isotopes has been described. Such multiple equilibrations are necessary because the separation factor per equilibration (ratio of the concentrations of the two isotopes in the resin divided by that ratio in the solution) is only about 1.013.

When a boric acid solution is percolated through an anion-exchange column containing hydroxide ions, $OH^-$, that are associated with the cationic fixed sites on the polymer gel, borate ions are exchanged for the hydroxide ions because of the favored formation of undissociated water molecules. As more boric acid solution is fed to the column, a wave or boundary, separating a borate region from a hydroxide region, moves down the column. The speed of the boundary is less than the linear velocity of the solution because the ions are more concentrated in the solid than in the solution. As the additional boric acid solution percolates over the borate-form resin in the lengthening borate region, the isotopic partition equilibrium is established.

Multiple equilibrations are achieved by terminating the feeding of the boric acid solution after a borate region of adequate length has been formed and then feeding a hydrochloric acid solution. When the hydrochloric acid solution contacts the borate-form resin, chloride ions from the solution are exchanged for borate ions because the weak (undissociated) boric acid is formed in the solution. As more hydrochloric acid solution is fed to the column, a wave or boundary, separating the lengthening chloride region from the borate region, moves down the column. The displaced borate ion, as boric acid, passes downward over the remaining borate region until it encounters the hydroxide region. Then, the borate ion is redeposited, forming water as described above. Thus, all the borate that is displaced at the rear boundary of the borate region is redeposited at the front boundary of the borate region. As more hydrochloric acid eluant is provided, the borate region migrated down the anion-exchange column; both boundaries move at the same speed so the length of the borate region remains fixed as the hydroxide region ahead is consumed and the chloride region behind lengthens.

As the borate/boric acid "refluxes" within the moving borate region, the $^{10}B$ accumulates near the rear of the region because this isotope is preferred by the resin; the $^{11}B$ accumulates near the front of the region. After the borate region has been eluted through about 75 region lengths, the subregion of original isotopic composition will have been consumed and replaced by a continuous isotopic composition gradient from nearly pure $^{11}B$ at the front of the borate region to enriched $^{10}B$ at the rear, the slope of this isotopic composition gradient being determined by mass transfer factors. As the borate region migrates out the bottom of the column, appropriate early fractions of the eluate will contain nearly pure $H^{11}BO_2$, the intermediate fractions will contain various intermediate isotopic mixtures which could be recycled for further treatment, and the later fractions will contain $HBO_2$ enriched in $^{10}B$. The chloride-form resin is regenerated to the hydroxide form by treating it with a strong solution of sodium hydroxide.

A similar displacement-chromatographic ion-exchange technique has been described for separating the lanthanide elements (the rare earths) on fixed-bed cation-exchange columns. The mixture of rare-earth ions is associated with the fixed anion sites on the cation-exchange resin, but the rare-earth ions are complexed in the aqueous solution with an organic chelating agent such as ethylenediaminetetraacetic acid (EDTA). The differences in the stabilities (degrees of dissociation) of the rare-earth/EDTA complexes provide the separation. The loaded rare-earth region is eluted with an aqueous solution of the triammonium salt of EDTA which displaces the rare-earth ions from the cation-exchange resin at the rear boundary to form the undissociated rare-earth/EDTA complexes; the ammonium ions are left on the resin forming a lengthening ammonium region. The aqueous solution of the rare-earth/EDTA complexes passes over the rare-earth region, allowing the relative resin-solution distribution equilibria to be established. At the front boundary of the rare-earth region, the rare-earth complexes encounter the cupric ion, $Cu^{+2}$, sorbed on the resin. Because the copper-EDTA complex is more stable than all the rare-earth/EDTA complexes, all the rare-earth ions are redeposited on the resin, replacing the $Cu^{+2}$ ions which form the Cu-EDTA complex in the solution.

As the rare-earth-ions/rare-earth-complexes reflux within the moving rare-earth region, the rare-earths which form the more stable complexes with EDTA accumulate at the front portions of the region; those that form the weaker complexes accumulate at rear portions of the region. Catching consecutive fractions of the aqueous eluate as the rare-earth region passes off the column will provide some nearly pure solutions of individual rare earths and some binary mixtures. The ammonium-form resin is regenerated to the cupric form by passing a solution of cupric sulfate through the column.

Another use of the displacement-chromatographic ion-exchange technique is for the separation of the isotopes of nitrogen. In this system the nitrogen isotopes are partitioned between the ammonium form of cation-exchange resin and ammonium hydroxide in solution. The ammonium region is eluted with a sodium hydroxide solution. The ammonium ions are displaced at the rear boundary because of the formation of the weak base, ammonium hydroxide. The ammonium ions are redeposited at the front boundary because of the formation of undissociated water molecules.

As the ammonium-ion/ammonium-hydroxide refluxes within the moving ammonium region, $^{14}N$ accumulates near the front of the region because this isotope favors the ammonium hydroxide solution; $^{15}N$ accumulates near the rear of the region because this isotope favors the ammonium ion on the resin. Catching proportionate fractions of the aqueous eluate as the ammonium region passes off the column will first provide a solution of ammonium hydroxide enriched in $^{14}N$, then an intermediate fraction of mixed composition for recycle, and finally a fraction enriched in $^{15}N$. The sodium-form resin is regenerated to the hydrogen form by passing a strong solution of sulfuric acid over the column.

The foregoing examples illustrate the utility of the general form of the displacement-chromatographic ion-exchange separation process. The separating region is eluted with an eluting ion in the form of a solution of a compound providing such ion. The rear boundary reaction deposits the eluting ion on the resin and forms a compound dissolved in the solution. Various species of the ion being processed are separated as such solution passes over the advancing separation region by what is conveniently called reflux processing. The front boundary reaction redeposits the ion being processed onto the ion exchange bed by displacing the retaining ion to form in the solution a compound of such retaining ion.

Early workers tried to separate the isotopes of uranium by eluting the uranyl ion, $UO_2^{+2}$, on cation-exchange resin with various eluant ions. While some minor separations were achieved, the separation factor was too low to be practicable. Larger separation factors were obtained by passing uranyl ions over resin in the uranous ion form.

When an aqueous solution of uranyl chloride encounters cation exchange bed containing uranous ion, the cation exchange equilibria tend to favor the concentration of the $U^{238}$ isotope as sorbed tetravalent uranous ions on the cation exchange bed and to favor enrichment of the $U^{235}$ isotope in the aqueous solution of hexavalent uranyl ions. A variety of procedures have been proposed relating to uranium enrichment using a cascade of a great many ion exchange beds because the maximum separation factor per theoretical stage (that length of bed required to establish the equilibrium isotopic partition) is only about 1.0007. The numerous earlier proposals were not sufficiently attractive to be industrialized.

Shimokawa et al, U.S. Pat. No. 3,511,620, describes a method in which granular particles of cation exchange resin gravitate through an exchange zone. The theoretical stage length is objectionably long in U.S. Pat. No. 3,511,620.

In Charlot et al, French Pat. No. 1,600,437, an initial portion of a fixed bed column is converted to a uranium region by treatment with uranous chloride solution. Such uranium region is chromatographically displaced by treatment with a ferric chloride solution. When the uranium region has been displaced to the bottom of the column, some enrichment of the boundary fractions has been accomplished by the oxidative displacement. An electrolytic apparatus is employed for oxidizing the ferrous effluent to ferric chloride and for reducing the hexavalent uranium solution to tetravalent uranium solution for resorption on the cation exchange bed. Significant back-mixing and inefficient utilization of the cation exchange beds are inherent disadvantages of the teaching of French Pat. No. 1,600,437.

The pioneer breakthrough was the invention of Dean B. James, disclosed in U.S. Pat. No. 3,869,536, derived from Ser. No. 88,904, filed Nov. 12, 1970, in which there was a reductive region ahead of the front boundary of the uranium region, whereby the uranium was reduced in situ; that is, within the bed. The James invention of uranous-uranyl chromatographic displacement is outstandingly superior to previous methods for uranium enrichment by cation exchange because the James method requires a shorter length of each theoretical stage of enrichment, sometimes called the height of a theoretical plate, or HTP, or a shorter HTP than prior procedures. The experimental examples described in the James application feature the use of a series of interconnected columns so that the liquid flows downwardly through columns piled on top of each other.

The James method of preparing composition having isotopic distribution of $U^{235}$ isotope and $U^{238}$ isotope different from the isotopic distribution of the uranium feedstock composition has been generically described as consisting of: providing a porous bed of cation exchange solid material, which bed remains in a predominantly fixed position relative to solution flow, the liquid treatment solutions being supplied at at least one feed zone and the solutions being withdrawn at at least one effluent zone, there being a large ratio of the length of the bed to the cross-section dimension of the bed, thereby promoting substantially plug flow of aqueous solutions, the cross-sectional characteristics of such flow not being adversely affected as the solutions advance along the length of the bed, there being at least sometimes a plurality of displaceable regions along the length of the bed, some of the chemical reactions occurring at the boundaries between adjacent regions of the bed, the front boundary of an advancing region being distinguished from the rear boundary and from the principal portion of an advancing uranium region; feeding a solution of a metal cation to provide a region of the bed in which the ion exchange sites are occupied predominantly by sorbed reducing metal cations capable of reducing dissolved hexavalent uranium to sorbed tetravalent uranium, such reducing metal region extending ahead of the uranium region so that the rear boundary of the reducing metal region is at the front boundary of the uranium region, said feeding being stoichiometrically equivalent to the hereinafter designated feeding of the oxidizing metal cation and being many times the stoichiometric equivalent of the tetravalent uranium sorbed on the cation exchange sites in the uranium region; feeding a solution of an oxidizing metal cation to provide an oxidizing metal region having a front boundary at the rear boundary of the uranium region, such feeding being a driving force for advancing the combination of the front boundary of the oxidizing metal region, the uranium region, and the rear boundary of the reducing metal region along the length of the bed by redox chromatographic displacement, such displacement predominantly occurring without significantly modifying the ratio of bed length to uranium region length, the rate of feeding of the oxidizing metal solution being controlled to promote said plug flow of aqueous solutions through the bed and the feeding of the oxidizing metal being continued for many hours, the feeding of the oxidizing metal ion being many times the stoichiometric equivalent of the tetravalent uranium sorbed in the uranium region, said feeding of the oxidizing metal cation being substantially stoichiometrically equal to the feeding of the reducing metal cation; withdrawing from the bed an aqueous solution containing a quantity of an oxidized form of the reducing metal cation corresponding to the amount of reducing metal cation fed to the bed; withdrawing from the bed an aqueous solution containing a quantity of a reduced form of the oxidizing metal cation, such reduced form being a lower valent form of the oxidizing metal cation; feeding a solution of hexavalent uranium compound susceptible of enrichment to provide a uranium region having a front boundary at the rear boundary of the reducing metal region, said uranium region having a rear boundary at the front boundary of the oxidizing metal region, the combination of the rear boundary of the reducing metal region, the uranium region, and the front boundary of the oxidizing metal region being adapted to advance by reductive chromatographic displacement along the length of the bed, the thus fed hexavalent uranium solution being subjected to reduction to tetravalent uranium sorbed on the cation exchange sites, such uranium reduction occurring at the boundary between the front of the uranium region and the rear of the reducing metal region, and the tetravalent uranium absorbed on the cation exchange sites being subjected to oxidation to hexavalent uranium cation in solution, such uranium oxidation occurring at the boundary between the rear of the uranium region and the front of the oxidizing metal region, such aqueous solution of hexavalent uranium generated within the cation exchange bed flowing from the rear boundary through the body to the front of the uranium region, and after the uranium region has advanced a length many times the cross-sectional dimension of the bed; withdrawing from the front and rear boundaries of the uranium region solutions of uranium compounds having an isotopic distribution different from that in the uranium solution fed to the bed.

SUMMARY OF THE INVENTION

The present invention features relative movement between the ion exchange bed and its chamber so that the displacement of the regions is accomplished while maintaining the boundaries stationary with respect to the chamber, so that solutions can be injected into and withdrawn through conduits penetrating the walls of the chamber. Such solutions enter or leave from the sidewalls of the elongated ion exchange bed, as distinguished from the conventional flow to the top and from the bottom surfaces of cylindrical ion exchange columns. The ion exchange treatment can be continuous. Although most of the flow of the solution of separating mixture of ions in the separation region represents reflux, a lesser amount is fresh feed, with continuous withdrawal from near the boundaries of the separation region of solutions having modified compositions, such withdrawal rates equaling the rate of fresh feed of solution of the original mixture of ions to the selected unit of a cascade of ion exchange units. In certain embodiments, the ion exchange bed has annular shape so that the relative movement between the bed and its chamber is achieved by rotation about the axis of such annular bed. In certain embodiments, enrichment of uranium ions by the method of said James method is conducted with relative movement between the ion exchange bed and its chamber.

The invention is further clarified by the description of certain of the embodiments shown in the drawings and the discussion of the concepts related thereto.

DESCRIPTION OF DRAWINGS

In the accompanying drawings.

DESCRIPTION OF PREFERRED EMBODIMENTS

In preferred embodiments of the present invention, the process described in the examples of said James application is utilized. Such process can be clarified by reference to the eight following equations:

A. titanous ion displaces cheap ion

B. uranyl ion displaces titanous ion

C. refluxing uranyl and uranous ions

D. ferric ion displaces uranous ion

E. cheap ion displaces metal ions

F. electrolytic regeneration of titanous ion

G. electrolytic regeneration of ferric ion

H. overall summary excluding regeneration

In the equations, Rz refers to the fixed anion site within the water-soaked cation exchange resin. Cations can be sorbed at each of a plurality of such singly charged sites. Thus, HRz indicates a site at which a hydrogen ion is located. $Rz_3Ti$ refers to a sorbed titanous ion. Similarly, $FeOHRz_2$ refers to a sorbed partially hydrolyzed ferric ion. $UOHRz_3$ refers to a sorbed tetravalent partially hydrolyzed uranous ion. Hexavalent uranium is soluble in acidic chloride solutions and is shown in the equations as $UO_2^{+2}$. The tetravalent titanium compound is also water soluble and is shown as the titanyl ion $TiO^{+2}$. The ferrous ion in the chloride solution is identified as $Fe^{+2}$.

The separation factor for the equilibrium between the sorbed uranous ion and an aqueous solution of the uranyl ion is of the magnitude of 1.0007. This is the equilibrium constant for equation (C) in which the right-hand arrow is larger than the left-hand arrow, thus indicating an equilibrium constant greater than one. The preferential distribution of the $U^{238}$ isotope on the uranous form of the cation exchange resin has been long recognized, but until the invention of said James application, appeared to be of merely scholastic interest.

As indicated in the equation (B), the sorbed titanous ion $TiRz_3$ is effective in reducing hexavalent uranium ion from $UO_2^{+2}$ to $UOH^{+3}$ and thereby forming the titanyl ion identified as $TiO^{+2}$. This very important reaction occurs at the boundary which constitutes the rear boundary of the titanium region and the front boundary of the uranium region. With respect to the cation exchange bed, the front boundary of the uranium region is being displaced forwardly as long as there is the forwardly moving supply of the uranyl chloride solution and as long as there is a titanium region ahead of such front boundary. Equation (B) can be treated as the reductive half of the uranium redox phenomena.

The equation identified as (D), whereby ferric ions in acidic chloride solution are employed for oxidizing and displacing the sorbed uranous ions from a cation exchange resin is well known and can be treated as the oxidative portion of the uranium redox phenomena. The ferric ions not only oxidize the uranous ions to uranyl ions but they also displace the uranyl ions into the advancing solution, leaving partially hydrolyzed ferric ions on the resin. The advancing solution also contains ferrous ions.

Equations (F) and (G) relate to the use of an electrolytic cell which supplies electrons (identified as $e^-$) and indicates the reduction of the titanyl ion to the titanous ion in the two outer chambers and the oxidation of ferrous chloride to ferric chloride in the inner chamber of an electrolysis system. The chambers are separated by ion exchange partitions through which anions such as chloride readily permeate.

Equation (E) symbolizes the regeneration of the ion exchange resin. First, the sorbed ferric ion is removed by treatment with aqueous hydrochloric acid. The sorbed titanyl ion is also displaced to form acidic resin, as shown in Equation (E). The thus regenerated hydrogen ion form resin is then available for treatment with titanous chloride solution as previously described in the discussion of equation (A). Some ferrous ion is also sorbed in using regenerated solutions, but its presence does not prevent the operativeness of the system. To the extent that effluent containing ferrous chloride in hydrochloric acid can be obtained from the bed, it is directed to the electrolytic cell for oxidation to regenerated ferric chloride. The hydrochloric acid effluent is regenerated in a still to provide concentrated hydrochloric acid and distilled water.

Figure 1:
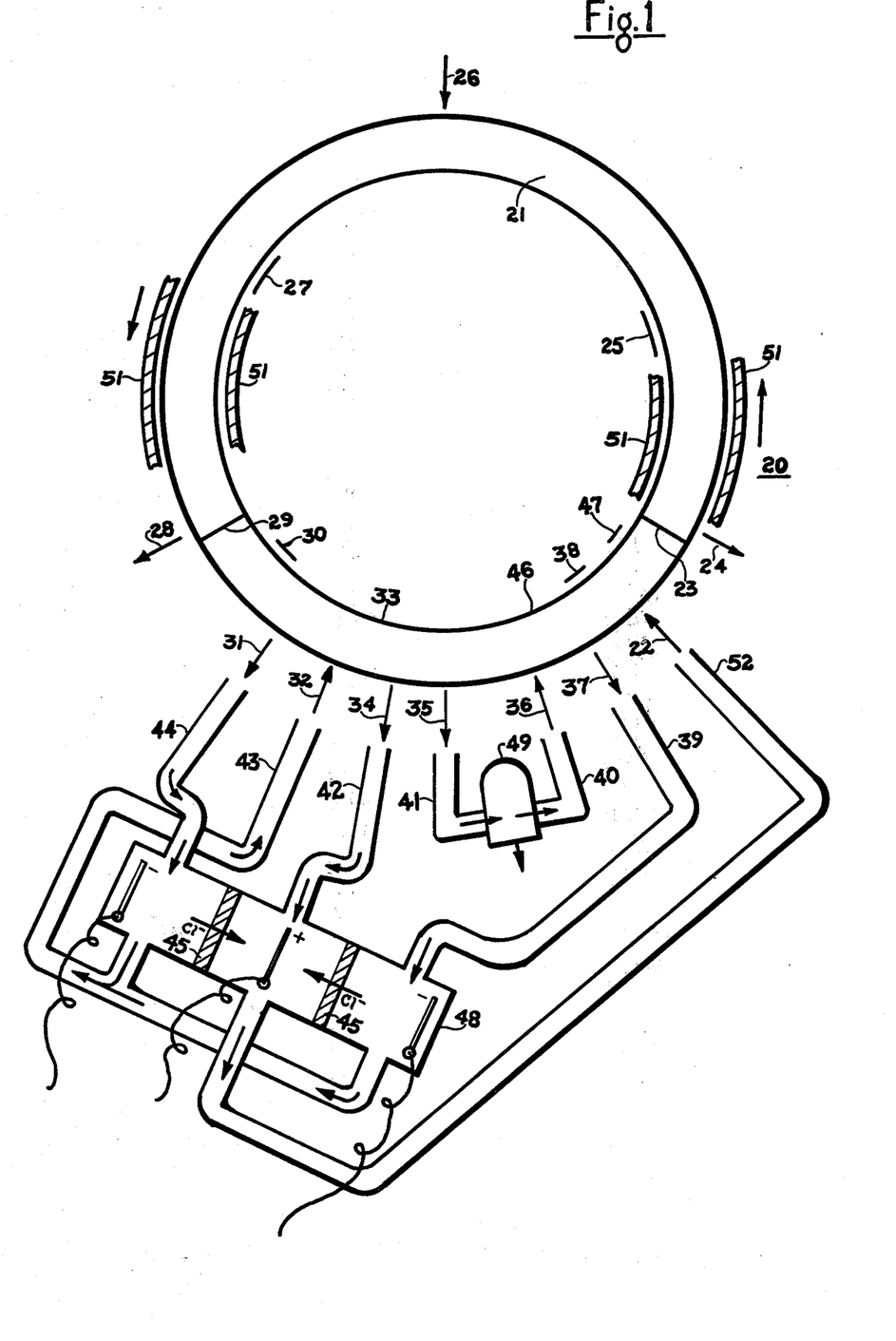
FIG. 1 is a schematic indication of a rotating annular chamber, there being a stationary annular bed in which the front and rear boundaries of the uranium region are stationary relative to said chamber and in which various solutions are withdrawn or injected along side portions of the annular bed of ion exchange material.
Figure 4:
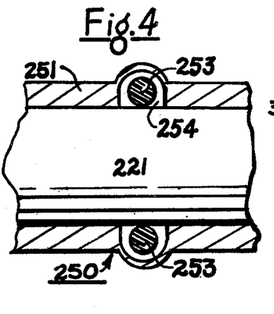
FIG. 4 is a schematic sectional view of a sealing zone of apparatus featuring the relative movement between an elongated ion exchange bed and its surrounding chamber, of the type shown in FIGS. 8, 3, and 2.

Referring now to the schematic diagram of FIG. 1, sub-system 20 of a uranium enrichment cascade system includes a stationary cation exchange bed 21 having a horizontally disposed annular shape. A snugly fitting annular chamber 51 rotates in a counterclockwise direction (top view) about a vertical axis, so that gravitational effects upon the liquid in the cation exchange bed are minimized. Between the stationary bed 21 and internal walls of portions of the rotating chamber 51 are a plurality of seals (see FIGS. 4 and 5) whereby the direction of flow of the aqueous solutions and/or the local pressure of such aqueous solutions in different zones can be carefully regulated. The flow between selected zones is thus precisely controlled.

Whether an annular bed has a circular cross section (in which case the bed is toroidal shaped) or a rectangular or other suitable cross sectional shape is predominantly for engineering consideration. If the bed is toroidal, then a sealing zone 250 of FIG. 4 can feature suitable gasketing means (e.g., an O-ring) 253 fitting against the toroidal wall of ion exchange bed 221 and restrained from linear shifting in groove 254 of chamber 251. If the bed has a rectangular cross section, then four or more linear gaskets can be yieldingly urged against the bed to provide the appropriate gasketing means 253 between bed 221 and chamber 251.

Figure 5:
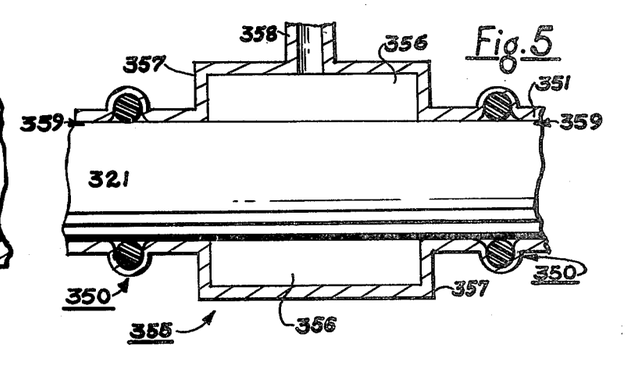
FIG. 5 is a schematic sectional view of a modifying zone of the apparatus of the type shown in FIGS. 2 and 8, featuring relative movement between an elongated ion exchange bed and its surrounding chamber.

In accordance with the present invention, an ion exchange bed has side walls through which liquid solutions are injected and withdrawn. As shown in FIG. 5, a modifying system 355 provides a liquid transfer zone 356 defined by an enlarged portion 357 of chamber 351, to which or from which liquid may flow through conduit 358. Aqueous solutions injected through conduit 358 are forced to mix with the liquid flowing near the core of bed 321 because sealing zones 350 (corresponding to the sealing zones 250 of FIG. 4) minimize any propensities for such injected solutions to channel through a wall zone 359 between bed 321 and the principal internal walls of chamber 351. Similarly, when modifying system 355 is employed to withdraw effluent, such stream is withdrawn from the core of bed 321 as well as from other portions of the cross section of bed 321. Modifying system 355 permits a body of solution at least substantially to surround the sidewalls of the ion exchange bed so that solutions may be withdrawn from or injected toward the sidewalls of the bed 321 without unmanageable distortion of the desired cross sectional flow patterns. The general practice of prior art technologists was to achieve the desired cross sectional flow patterns by vertically aligned segments of ion exchange bed and modifying the composition of solutions by withdrawing solution only at the bottom of a segment and injecting solutions only at the top of a segment. Although the ratio of length to a cross sectional dimension is relatively low in appropriate modifying zones 355, the cross sectional distortion (non-uniformity of mixing at various distances from core) is sufficiently small to make the overall process manageable. Each modifying zone permits flow of solutions between the core of the bed and the liquid transfer zone 356 adjacent the sidewalls of the bed 351 without unmanageable distortion of the desired cross sectional patterns of the liquid flow along the length of the bed.

The clockwise and counterclockwise directions in FIG. 1 are related to viewing the system from above. A solution of ferric chloride is injected at zone 22 with sufficient pressure to direct the solution counterclockwardly toward the rear boundary 23 of uranium region 25. At such boundary 23 and uranium region 25, the ferric chloride oxides the tetravalent uranium sorbed on the ion exchange bed 21, dissolves the uranium as hexavalent uranium, and an aqueous solution comprising both $UO_2Cl_2$ and $FeCl_2$ flows counterclockwardly from the boundary 23 toward a principal portion 25 of the uranium region. Such reaction at boundary 23 is shown in Equation (D). The forward movement of the regions is counterclockwise. The solutions are moving forwardly at a faster speed than the forwardly moving regions. The chamber 51 is rotating counterclockwise at the same forward speed as the regions so that there is no relative movement between the region boundaries and the chamber 51.

As indicated by Equation (C), the isotope enrichment occurs by reason of the exchange between the aqueous solution of hexavalent uranium and the sorbed tetravalent uranium, which isotope exchange phenomena is predominantly concerned with the liquid "refluxing" through the uranium region as a result of the redox reactions at its boundaries. After the ion exchange enrichment process has been conducted for a sufficiently long period of time, such refluxing can be supplemented by the continuous feeding of a hexavalent uranium solution at a suitable central zone indicated at feed injection zone 26. Although the schematic diagram indicates that such injection of uranium feed can be near a midpoint between the two boundaries, there would be advantages, based upon analogies to distillation, to injecting the feed at a location at which the refluxing liquid most nearly matched the isotopic composition of the feed. Such concentrations would vary in accordance with the relative position of the separation sub-system in the cascade of similar separation sub-systems.

The refluxing solution of aqueous solution of uranium oxychloride advances forwardly and counterclockwise through the forward portion 27 of the uranium region and to the boundary 29 between the titanium region 30 and uranium region. At the boundary 29 the reaction identified by Equation (B) occurs, so that the uranium region is there lengthened at the same speed at which the uranium region is consumed by the oxidation reaction at boundary 23 and at the same speed at which the titanium region 30 is consumed. The aqueous solution flowing forwardly from zone 22 through boundary 23, through zones 25 and 27 of the uranium region, and through boundary 29 continues to flow counterclockwise through at least a portion of the titanium region 30. Such solution contains not merely the ferrous chloride formed at boundary 23, but also the titanium oxychloride formed at boundary 29. Such aqueous solution is withdrawn toward conduit 44 through modifying zone 31. Thus, there is a pressure drop between zone 22 where the ferric chloride is injected to zone 31, from which the aqueous solution comprising ferrous chloride is withdrawn. Aqueous solution comprising titanium trichloride is injected at modifying zone 32 through conduit 43 at carefully regulated pressure conditions assuring rearward (or clockwise) flow for maintaining the rear boundary of titanium region 30 precisely at the selected location 29 and for maintaining the front boundary of the titanium region 30 at a location adequately rearward of ferrous chloride withdrawal zone 34. The injected titanous ions are sorbed on the resin to provide such titanium region 30. A pressure adjustment sealing zone 33 may, if desired, be provided between the titanous injection zone 32 and ferrous chloride withdrawal zone 34.

The effluent from modifying zone 34 through outlet 42 can include both the displaced ferrous chloride solution and any excess solution resulting from injection of excess solution in the regeneration zone extending from boundary 29 forwardly to sealing zone 38. During start-up with a pure hydrogen form ion exchange bed 21, and also under appropriate conditions at other times, titanium trichloride can be injected at a plurality of sites symbolized generally by 43. The exact placement of zones of injection and zones of withdrawal can be modified to meet appropriate engineering requirements. The schematic drawing of FIG. 1 should be interpreted as recommending the use of a suitable number of injection sites and a suitable number of effluent withdrawal sites to meet the needs of the ion exchange system.

Hydrochloric acid can be introduced as an aqueous solution at injection conduit 40 in zone 36, whereby sorbed metal ions (titanium, iron, and uranium) are displaced from hydrogen region 46 of bed 21, which region is converted fully to the hydrogen ion condition. Solutions containing metal ions are withdrawn through conduit 42 in zone 34 and through conduit 39 in zone 37. Dilute acid is removed at an appropriate location such as withdrawal conduit 41 in zone 35. A selected zone of the bed, conveniently designated as hydrogen region 46, is thus converted to a predominantly hydrogen ion condition near a pressure sealing zone 38. Dilute hydrochloric acid is concentrated in a still 49; and the water is separated and may, if desired, by recycled to any of the zones for aqueous solution injection.

The effluent withdrawn at zones 31, 34, and 37 can be directed through conduits 44, 42, and 39, respectively, to a system 48 for the electrolytic purification and recycle of such effluent components. As indicated by Equations (F) and (G), the effluent can be subjected to a multi-chamber electrolytic operation for the preparation of an aqueous solution of titanium trichloride and an aqueous solution of ferric chloride which can be recycled to zones 32 and 22, respectively. Chloride permeable membranes 45 separate an anode chamber from a cathode chamber, the reduction of the metal ions occurring in the cathode chamber.

As shown in FIG. 1, there can be the continuous uranium withdrawal zones 28 and 24, adjacent the boundaries 29 and 23 respectively, of fractions which have undergone modification of isotope distribution. It is convenient schematically to indicate the enrichment of $U^{235}$ at zone 28 and to show the depleted stream withdrawn at zone 24, in accordance with the boundary principles discussed in the James application. Various diffusion factors, porosity of the ion exchange bed 21, and related phenomena affect the enrichment phenomena. As indicated in certain examples of the James application, inadequate control of diffusion factors can lead to $U^{235}$ enrichment at each of the two boundaries instead of at only one of the boundaries. However, in a cascade system of the type herein described, both depletion and enrichment must be achieved to provide a competitively attractive process. Hence, engineering controls of flow rates, pore size of macropores in the particles of ion exchange resin, and related diffusion factors, are regulated to assure such enrichment of $U^{235}$ at zone 28 and such depletion of $U^{235}$ at zone 24. It is generally desirable to withdraw proportions of liquid corresponding to the enrichment achieved by the two product streams. Of importance, the total rate of withdrawal of uranium compounds from zones 24 and 28 is substantially equal to the rate of supply of uranium compounds in the feed at zone 26. Moreover, the rate of feeding the uranium solution to zone 26 is advantageously controlled to be less than about 10 per cent of the stoichiometric rate of the refluxing uranium solution, which rate is derived from the rate of feeding the redox solutions at zones 22 and 32.

It should be noted that the annular bed 21 of ion exchange resin has a large uranium region 25 and 27, the front of the region being at boundary 29; and the rear of the region being at boundary 23. A solution of ferric chloride is injected at zone 22, flowing through boundary 23 and thus actuating the flow of liquid through the uranium region to the boundary 29. Such aqueous solution at boundary 29 reacts with the titanous ion sorbed on the ion exchange resin in the titanium region 30 whereby the boundary 29 between the uranium region and titanium region 30 advances at a speed which is significantly less than the speed of the advancing aqueous solution. The aqueous solution is withdrawn at zone 31 after passing through only a small portion of the titanium region 30. Such withdrawn solution includes ions of ferrous iron and titanium in a tetravalent condition. An aqueous solution of titanous chloride is injected at zone 32 and flows rearwardly to maintain the boundary 29 at a relatively fixed location with respect to chamber 51, which rotates counter-clockwise at the same speed as the region migration speed. Regenerated concentrated hydrochloric acid is injected at zone 36, thereby forming a hydrogen region 46 in the resin bed. The hydrogen displaces additional amounts of metal ions. A solution comprising titanium oxychloride can be withdrawn at zone 37 through conduit 39. A sealing zone 38 may be interposed between the metal ion effluent zone 37 and the ferric chloride injection zone 22. The regenerated ferric chloride solution may be withdrawn from electrolytic regeneration system 48 and directed toward ferric chloride injection zone 22 through conduit 52. In the operation of the separation method, the aqueous solutions comprising solubilized iron flow counterclockwise to boundary 23, at which uranium is displaced from the ion exchange bed 21 into the counter currently flowing aqueous solution. As such aqueous solution flows counterclockwise in the ion exchange bed, from boundary 23 to boundary 29, the important ion exchange reaction occurs, whereby the proportion of 235 uranium isotope increases in the aqueous solution and the proportion of 235 uranium isotope decreases in the ion exchange resin. At boundary 29, the reaction of the solution with the region containing trivalent titanous ion sorbed on the ion exchange bed leads to the deposition of the uranium content of the aqueous solution at boundary 29 and the solubilizing of the titanium as tetravalent titanium oxychloride. Zone 28 is immediately adjacent such boundary 29 so that a stream of aqueous solution comprising dissolved uranium can be withdrawn as the desired enriched product from the process. Similarly, an aqueous solution of a uranium compound containing depleted amounts of the 235 uranium isotope can be withdrawn at 24 and directed to appropriate other separation sub-systems in the cascade of separation units.

Figure 2:
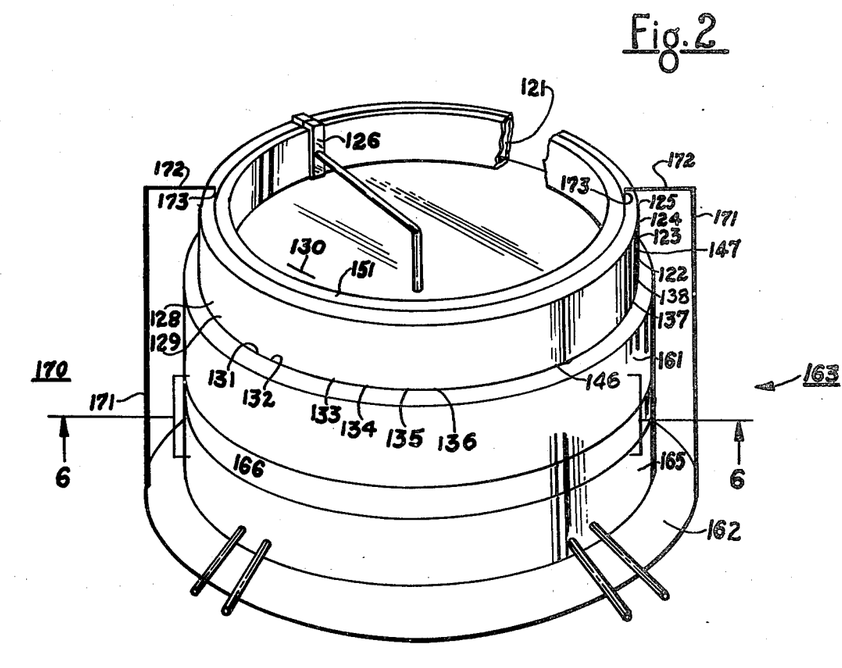
FIG. 2 is a perspective view of one embodiment of apparatus featuring the concept of FIG. 1, there being a rotating annular chamber within which a stationary annular ion exchange bed has a rectangular cross section.
Figure 3:
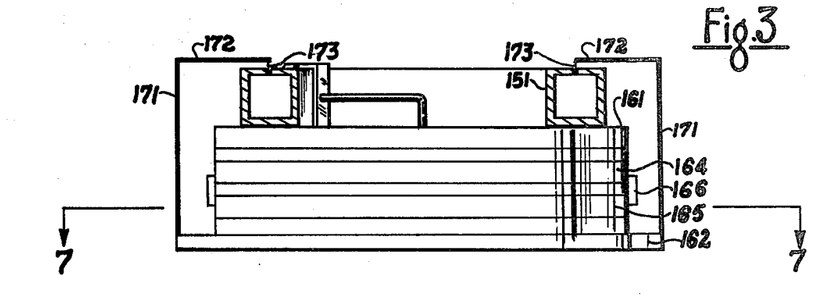
FIG. 3 is a schematic sectional view of an apparatus having a method of operation resembling that of FIG. 2.

The operation of the apparatus of FIG. 2 is clarified by the previous discussion of the schematic flow sheet of FIG. 1. As shown in FIG. 2, an annular-shaped ion exchange bed 121 fits snugly within a chamber 151 having a plurality of seals whereby the liquid pressure in various zones may be maintained at different pressures. The chamber 151 rotates counterclockwise about the vertical axis of the annular stationary bed 121. The ferric chloride can be injected at a ferric chloride injection site 122, thus providing a sorbed iron region 147 in bed 121. In sealing zone 138, suitable seals minimize any flow of ferric chloride solution in a clockwise direction, while permitting the ferric chloride solution to flow in the counterclockwise direction. Any of the ferric chloride solution flowing past the seals in sealing zone 138 will be withdrawn through effluent zone 137. The rear boundary 123 of uranium region 125 is also the front boundary of the iron region 147. Such boundary 123 is not troublesomely fuzzy because the liquid flowing through the boundary 123 is precisely regulated to achieve non-turbulent plug flow.

Similarly, the withdrawal of the very small amount of product solution of uranium oxychloride at zone 124 is also adjusted to preserve plug flow conditions, said solution containing depleted proportions of the $U^{235}$ isotope. The withdrawal of the two product streams at zones 124 and 128 are carefully maintained to equal the rate of supply of the uranium feed at zone 126, the site for injection of a solution of hexavalent uranium oxychloride.

The cascade of sub-systems is not designed to recover $U^{235}$ isotope of more than 90 per cent purity; and accordingly, has little interest to those desiring explosive grades of uranium. The cascades are designed to produce fuel grade uranium, so the feed has a concentration of the $U^{235}$ isotope less than desired for use as nuclear fuel. Certain types of nuclear fuel contains about 20 per cent special nuclear material such as $U^{235}$. Other procedures appear to offer technological advantages for enriching intermediates such as 90 per cent $U^{235}$ to substantially pure special nuclear material.

A sharp boundary is maintained at zone 129 because the solution of uranium oxychloride flowing counter-clockwise from boundary 123 through the uranium region 125 to the boundary 129 represents smooth plug flow. An aqueous solution of titanous trichloride is injected at zone 132 to provide the titanium zone 130. Because the regions are advancing forwardly counterclockwise, the titanous chloride injection can be deemed a rearward injection inasmuch as the injection zone 132 is forward of the boundary 129 between the uranium region and titanous region 130. An aqueous solution comprising titanium oxychloride and ferric chloride (but substantially free from uranium compounds) can be withdrawn at effluent zone 131.

The titanous cations sorbed on the ion exchange bed 121 by said rearward injection at 132 and not oxidized at the boundary 129 can be leached from the bed by treatment with an aqueous solution of hydrochloric acid injected at zone 136. An aqueous solution comprising metal compounds and hydrochloric acid (anabsorbed in the displacement forming hydrogen region 146) can be withdrawn at effluent zone 137. The chamber 151 has any suitable combination of injection sites, water rinsing injection sites, and effluent withdrawal sites between the titanous region 130 and iron region 147, the engineering for the regeneration regions being more complex than for the isotope enrichment region. The schematic showing of a hydrochloric acid injection site 136 and effluent sites 131, 134, 135, and 137 is merely a schematic showing of the regeneration of the bed 121 as the chamber 151 rotates through an arcual segment of bed 121 corresponding to titanium region 130 to iron region 122. The effluent from zones 131, 134, 135, and 137 can be reprocessed in appropriate systems to provide solutions suitable for recirculation.

Figure 6:
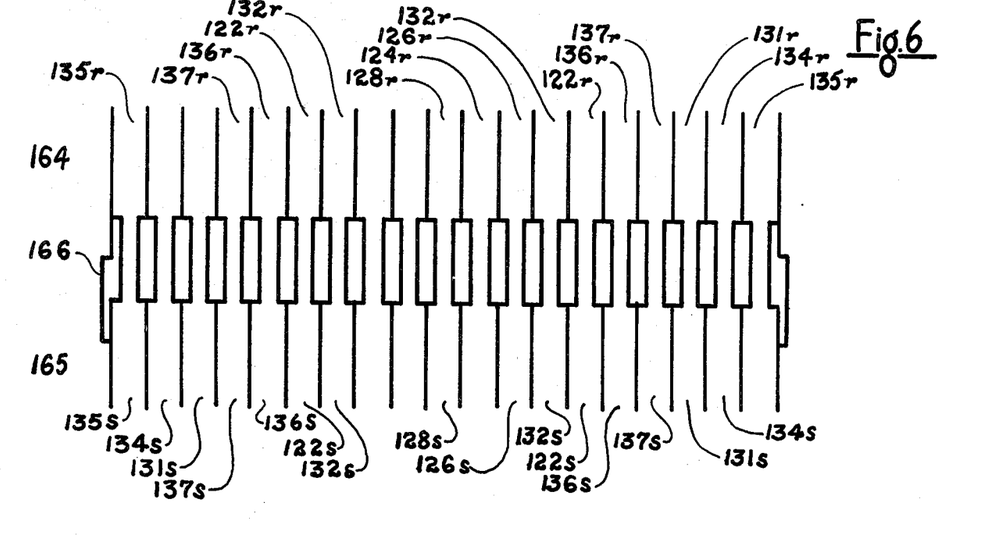
FIG. 6 is a schematic sectional view of a portion of a rotating conduit zone of the apparatus of FIG. 2, taken on line 6—6 of FIG. 2.
Figure 7:
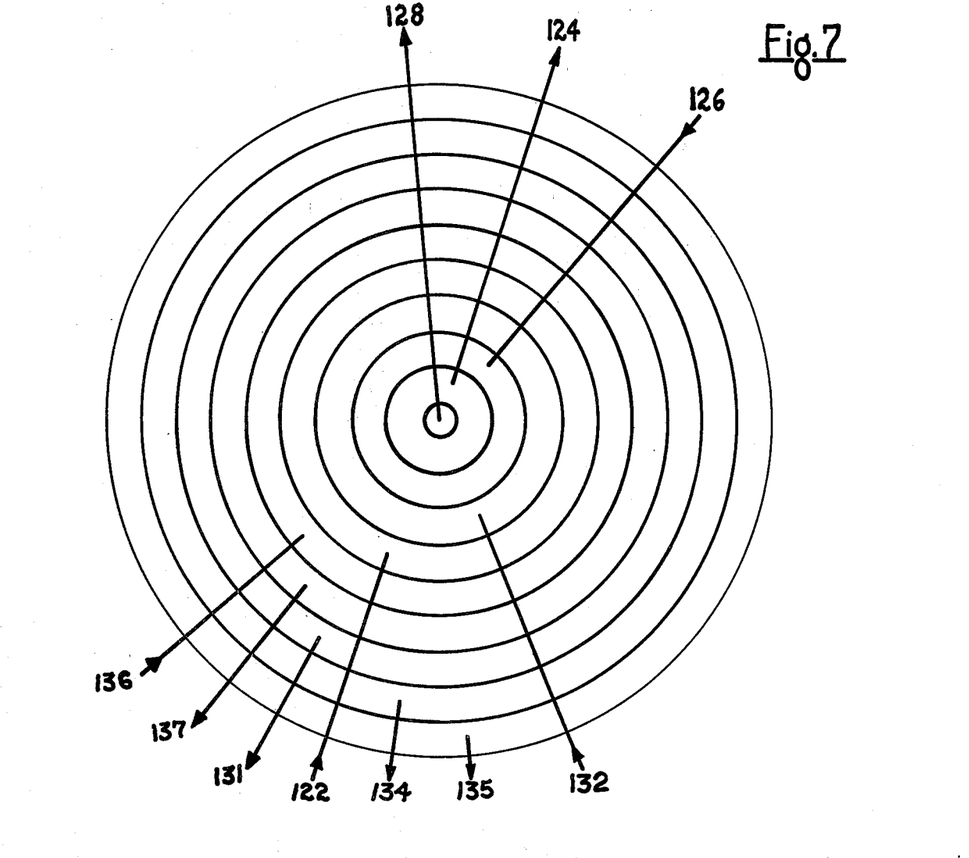
FIG. 7 is a schematic view of a portion of a rotating conduit zone of an apparatus of FIG. 3, taken on line 7—7 of FIG. 3.

Rotating chamber 151 can be mounted upon a disc 161 rotatingly supported ultimately a base 162. Rotary sealing means 163 permits a plurality of annular conduits (see FIG. 7) in disc 161 to be in communication with corresponding annular conduits in base 162. A rubber type gasket 166 (See FIG. 6) can serve as a rotary seal for such sealing means system 163. Engineering modifications of the rotary seal system for minimizing any backmixing and maximizing plug flow of the pertinent solutions can be made without departing from the simplified schematic views of the drawings. The annular conduits are conveniently identified by the zones of bed 121 with which they are connected, using, for example, 122 $r$ for the rotating conduit supplying a solution of ferric chloride and 122 $s$ for the stationary annular conduit in the base. FIGS. 6 and 7 clarify such supply of stationary solutions to the rotating chamber 151 of FIG. 2.

A plurality of supports 170 (FIG. 2) comprising a post 171, bar 172, and pin 173 support the stationary annular bed 121 from the base 162. The feed can be deemed to flow through annular conduit 126 $s$ in stationary base 162, through an opening $p$ in gasket 166, through rotating conduit 126 $r$ and to feed zone 126 of bed 121. Similar paths are followed by other aqueous solutions.

Figure 8:
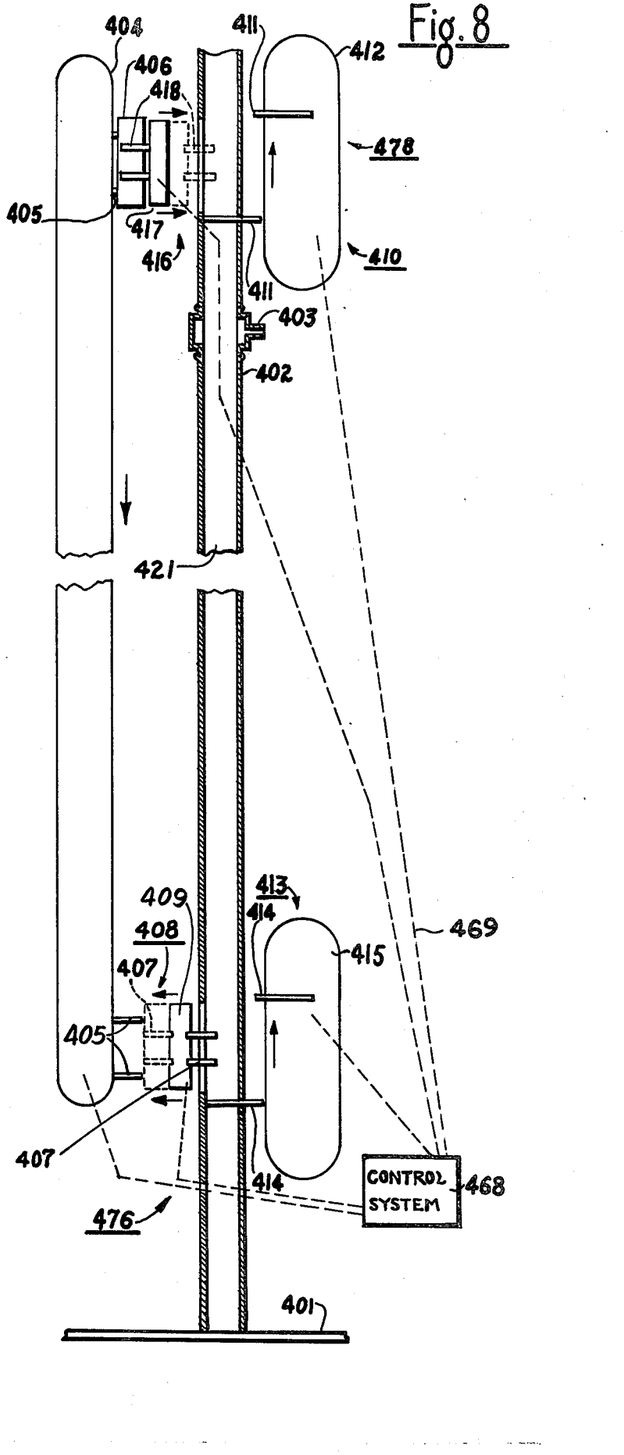
FIGS. 8 and 9 are schematic views of an embodiment of the invention featuring a vertical column, and are related to each other analogously to FIGS. 1 and 2.

FIG. 8 is a schematic showing of apparatus for automatically advancing upwardly a stack of cylindrical ion exchange units 406, such units functioning as a vertical column type of ion exchange bed 421. A chamber 402 has a vertical cylindrical opening through which the stack of units 406 of the bed 421 is advanced upwardly. At appropriate locations along the upward path of the ion exchange units, there are modifying zones 403 corresponding to the modifying zones 355 of FIG. 5. Particular attention is directed to the fact that solutions are injected into and withdrawn from chamber 402 at the side walls of units 406, and without any solutions being injected into or withdrawn from the end walls of such ion exchange units.

A lifting device 413 and a downward pressure device 410 cooperate to maintain the stacked units 406 in contact with each other and to advance upwardly at a controlled speed. The lifting device 413 is provided with retractable fingers 414 secured to an endless chain 415 so that an ion exchange unit 406 can be inserted between a pair of upper and lower fingers 414 and advanced upwardly, the upper finger 414 being retracted as soon as the unit 406 is appropriately aligned for such upward movement. Thereafter, only the lower retractable finger 414 supports and lifts the stack of units so that the column 421 advances upwardly at a controlled speed.

The pressure device 410 closely resembles the support device 413 and comprises a pair of retractable fingers 411 secured to an endless chain 412. A retractable finger 411 is inserted between two units of the columnar stack of ion exchange units as soon as the bottom of a unit 406 enters the zone of regulation by the pressure device 410. Such pressure device helps preserve the stack of ion exchange units 406 until the time when the ion exchange bed 421 has advanced upwardly enough to permit another retractable finger to start serving as a pressure means.

An upper shuttle 416 has fingers 418, a pair of which grip a unit 406 as soon as it is lifted into isolation from the stack of units. The fingers 418 on the upper shuttle pick up the ion exchange unit 406 and subject it to the flip-flop action of a flip-flop 417 so that the fingers 418 can transfer the ion exchange unit 406 to fingers 405 of an endless conveyer chain 404. Such transfer occurs within an unloading zone 478. After the upper shuttle 416 has made its stroke from the position adjacent the chamber 402 to the position adjacent the conveyer chain 404, the endless conveyer 404 lowers a unit 406 to a lower position from which it is removed by fingers 407 on lower shuttle 408 having a flip-flop 409 so that the unit is transferred from downwardly moving conveyer 404 to chamber 402 in a loading zone 476.

A control system 468 regulates the operation of downward pressure device 410, lifting device 413, upper shuttle 416, endless conveyer chain 404, and lower shuttle 408 to assure the maintenance of the stack of ion exchange units 406 in upwardly moving ion exchange bed 421. Communication lines 469 associate the sensor stations and actuation zones with control system 468. In modifications of the structure shown schematically in FIG. 8, suitable accumulation zones for ion exchange units 406 can be provided at either the upper and/or lower ends of chamber 402. Of importance, the ion exchange bed 421 is pushed upwardly through chamber 402 at a speed corresponding accurately to the speed of migration of the boundaries in bed 421. Suitable color detection means can be employed to provide signals actuating the control system 468 for assurance that the positions of boundaries within ion exchange bed 421 relative to appropriate modifying zones 403 of chamber 402 are relatively stationary.

Figure 9:
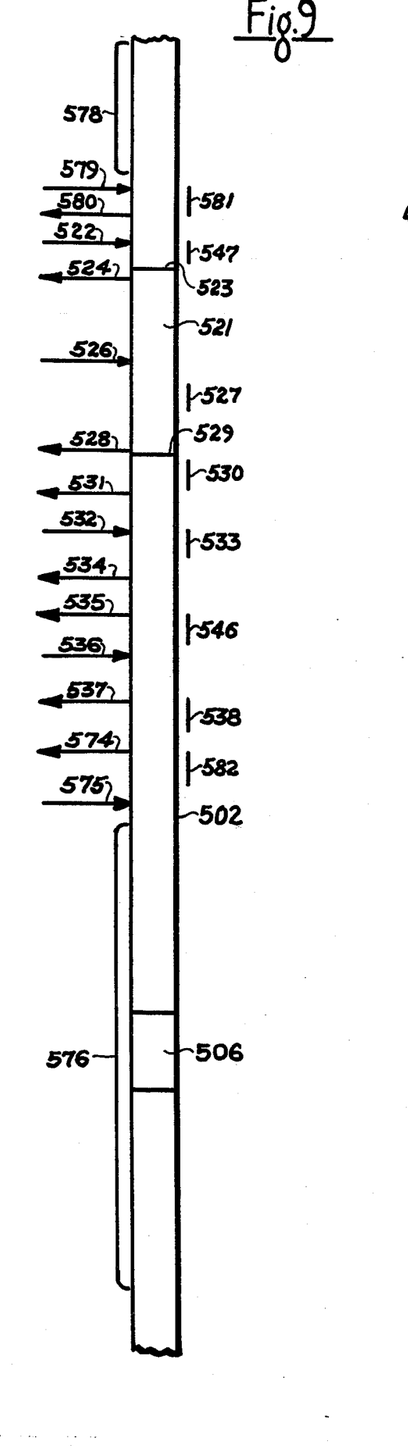

The schematic drawing of FIG. 9 shows zones of a vertical ion exchange bed column 521 in apparatus functioning to achieve the objectives of the apparatus of FIG. 8.

The schematic diagram of FIG. 9 shows the operation of the upwardly advancing ion exchange bed 521. Units of ion exchange material 506 are moved downwardly on a conveyor from a transfer zone 578 to a transfer zone 576 where they are loaded into the stack of units 506 constituting the bed 521. The stack assembly moves upwardly at a controlled rate adapted to maintain boundaries 523 and 529 at precise locations relative to chamber 502. Air is injected along the side walls of bed 521 at an upper injection zone 579 and withdrawn through effluent zone 580 in air region 581. If desired, the air withdrawn through zone 580 may be directed through a pump and recirculated to air injection zone 579. The pressure maintained in zone 581 is sufficient to decrease the likelihood of liquids flowing above zone 581, thus providing further safeguards for transfer zone 578.

It should be particularly noted that the ferric chloride injected at zone 522 is injected into the side walls of ion exchange bed 521 as distinguished from being directed onto the top surface of such bed. A portion of the ferric chloride is sorbed on the ion exchange bed and a portion of the solution flows downwardly to boundary 523 whereby the uranium is displaced and dissolved and whereby the boundary between iron region 547 and uranium region 527 is modified by moving downwardly (relative to bed 521) at the same speed as bed 521 is moving upwardly, thereby maintaining boundary 523 stationary with respect to chamber 502. The transfer systems 576 and 578 are advancing the ion exchange bed 521 upwardly at the same speed at which each region and each boundary tends to migrate downwardly. The aqueous solutions continue to flow downwardly.

An amount of feed is injected at zone 526 which constitutes only about 10% of the down-flowing liquid so that most of the flow of the uranium solution in uranium region 527 is reflux, with only a minor amount of fresh feed. A solution of uranium compound having a depletion of $U^{235}$ and an increase in the concentration of $U^{238}$ is withdrawn at zone 524. Similarly, an aqueous solution of uranium compound having an enriched concentration of $U^{235}$ is withdrawn through product withdrawal line 528.

At boundary 529 the downflowing aqueous solution encounters titanium region 530, the upper boundary of which 529 is maintained at a very precise location. A significant portion of the downflowing solution, comprising a mixture of ferrous chloride and titanyl oxychloride is withdrawn through effluent zone 531. Regenerated solution of titanium trichloride, or other trivalent titanous compound is injected at 532. In order to minimize the flow of titanous chloride solution downwardly and to provide an effective control of the fluid in the bed, a sealing zone 533 is immediately beneath the titanous chloride injection zone 532. If desired, a solution may be withdrawn, directed through a pump, and injected back into the sealing zone to help maintain a slight hydrostatic pressure in sealing zone 533.

An aqueous solution of ferrous chloride is withdrawn through withdrawal zone 534. A dilute solution of hydrochloric acid is withdrawn through zone 535. The ferrous chloride withdrawn through ferrous chloride withdrawal zone 534 may be electrolytically regenerated and supplied to iron injection zone 522. The dilute aqueous hydrochloric acid withdrawn at line 535 can be concentrated to provide concentrated hydrochloric acid injected at several sites, identified as 536. Metal ions such as iron and titanium can be withdrawn through zone 537 and the ion exchange bed 521 is thereby converted into a hydrogen region 546.

An air pressure zone 582 is maintained above transfer zone 576 whereby none of the liquid flows into the transfer zone 576. In ferric chloride injection zone 522, the pressure of injection is sufficient to assure the maintenance of the boundary 523 at the desired location notwithstanding the fact that the upmoving ion exchange bed 521 encounters the ferric chloride injection 522 above the boundary 523.

Particular attention is directed to the fact that the boundaries 523 and 529, as well as the zones for injection and effluent are maintained stationary relative to the regions of the ion exchange bed, even though there is the relative movement between the ion exchange bed 521 and chamber 502. The rate of speed of the migration of the regions corresponds exactly to the upward speed of the units of ion exchange bed 521.

Figure 10:
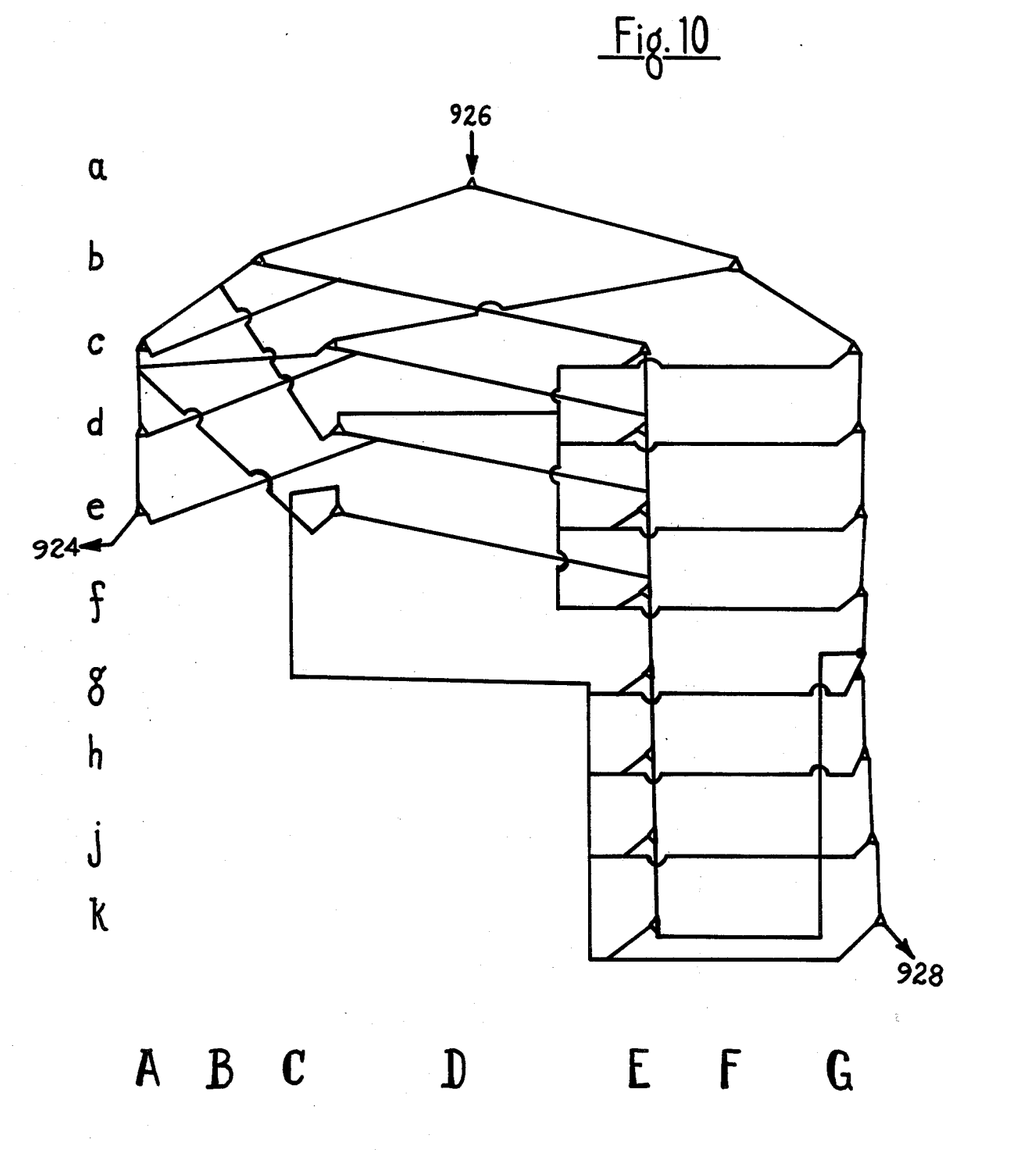
FIG. 10 is a schematic flow sheet of separation facility in which solutions are purified and recirculated through a cascade of ion exchange enrichment units.

FIG. 10 is a schematic showing of a cascade of sub-systems for the separation of uranium isotopes. A solution containing natural uranium is supplied as feed at line 926 and undergoes a series of ion exchange steps of isotope separation, the diagram of FIG. 10 showing a cascade of about 25 sub-systems. A sample benefitting from about ten stages of $U^{235}$ enrichment is withdrawn from line 928. From line 924 is withdrawn a stream having about five stages of depletion of $U^{235}$. Any enrichment process is most economical at isotope separations approaching equal concentrations. Any other suitable arrangement of cascades is appropriate in using the sub-systems of ion exchange enrichment of the present invention.

The continuous separation of fractions benefitting from displacement phenomena (previously attainable only on a batch basis) is attainable in the ion exchange sub-system of the present invention without regard to the choice of appropriate chemical reactants. All of the purifications discussed hereinabove are manageable in the present invention. The description of uranium isotope separation is merely illustrative of the use of chromatographic displacement in an ion exchange bed to effect a separation or a mixture.

It is claimed:

1. In a method in which an ion exchange bed is employed for modifying the isotope distribution in aqueous solutions of uranium compounds by preferential sorption rates in an ion exchange bed having a significant length relative to a cross sectional dimension, there being a plurality of regions along the length of said ion exchange bed, one of said regions being a uranium isotope separation region, the improvement which consists of:

maintaining the ion exchange bed as an annulus;

surrounding the annulus-shaped ion exchange bed with a chamber having a plurality of modifying zones in which aqueous solutions are withdrawn, injected, or pressurized, each modifying zone permitting flow of solutions between the core of the bed and the liquid transfer zone adjacent the sidewalls of the bed without substantial distortion of the desired cross sectional patterns of the liquid flow along the length of the bed;

withdrawing from a zone adjacent the front boundary of said uranium isotope separation region, a solution containing increased concentrations of ions of the 235 uranium isotope, such increased concentration being attributable to chromatographic displacement phenomena and such solution withdrawal being from side walls of the annular ion exchange bed;

withdrawing from a zone adjacent a rear boundary of the uranium isotope separation region a solution containing a controlled decreased concentration of ions of the 235 uranium isotope, such decreased concentration being attributable to chromatographic displacement phenomena, such solution withdrawal being to side walls of the ion exchange bed;

feeding to an intermediate portion of the uranium isotope separation region a stream of a solution containing mixture of ions of uranium isotopes at a rate totaling the rates of withdrawal from said boundaries, the total liquid flow through the uranium isotope separation region being several times said rate of feeding the mixture to be separated, the large ratio of total liquid flow to feed flow in the separation region being attributable to chromatographic displacement phenomena, such solution feeding being to side walls of the ion exchange bed;

supplying to a region in advance of the uranium isotope separation region a solution of trivalent titanium compound for the maintenance of an appropriate chemical reaction at the constantly advancing front boundary of the uranium isotope separation region;

supplying to the region rearward of the uranium isotope separation region a solution of ferric chloride, a portion of which solution flows forwardly to provide a chemical reaction at the rear boundary of the constantly advancing uranium isotope separation region, the length of the separation region remaining substantially constant because the migration speeds of the front and rear boundaries are substantially identical;

supplying regeneration solution to a regeneration region of the length of the ion exchange bed, whereby each portion of the length of the ion exchange bed may be repetitively used;

said solutions being supplied to maintain the speed of migration of the boundaries of the uranium isotope separation region at a controlled speed; and controlling the relative speed of movement between the length of the annular ion exchange bed and its surrounding chamber to be exactly equal and opposite to the migration speed of the boundaries, whereby the relative positions of the chamber and the boundaries is maintained stationary, and whereby the injection of solutions and withdrawal of solutions is constantly accurate notwithstanding such relative migration of boundaries along the length of the annular ion exchange bed and such relative movement between the annular ion exchange bed and its surrounding annular chamber.

2. In a method in which an ion exchange bed is employed for separating a mixture by preferential sorption rates in an ion exchange bed having a significant length relative to a cross sectional dimension, there being a plurality of regions along the length of said ion exchange bed, one of said regions being a separation region, the improvement which consists of:

surrounding the ion exchange bed with a chamber having a plurality of modifying zones in which solutions are withdrawn, injected, or pressurized, each modifying zone permitting flow of solutions between the core of the bed and the liquid transfer zone adjacent the sidewalls of the bed without substantial distortion of the desired cross sectional patterns of the liquid flow along the length of the bed;

withdrawing from a zone adjacent the front boundary of said separation region, a solution containing increased concentrations of ions of a selected component of said mixture, such increased concentration being attributable to chromatographic displacement phenomena and such solution withdrawal being from side walls of the ion exchange bed, there being no liquid flow to or from end walls of the ion exchange bed;

withdrawing from a zone adjacent a rear boundary of the separation region a solution containing a controlled decreased concentration of ions of said selected component, such decreased concentration being attributable to chromatographic displacement phenomena, such solution withdrawal being to sidewalls of the ion exchange bed, there being no liquid flow to or from end walls of the ion exchange bed;

feeding to an intermediate portion of the separation region a stream of a solution containing the mixture of ions to be separated at a rate totaling the rates of withdrawal from said boundaries, the total liquid flow through the separation region being several times said rate of feeding the mixture to be separated, the large ratio of total liquid flow to feed flow in the separation region being attributable to chromatographic displacement phenomena, such solution feeding being to side walls of the ion exchange bed, there being no liquid flow to or from end walls of the ion exchange bed;

supplying to a region in advance of the separation region a solution for the maintenance of an appropriate chemical reaction at the constantly advancing front boundary of the separation region;

supplying to a region rearward of the separation region a solution, a portion of which solution flows forwardly to provide a chemical reaction at the rear boundary of the constantly advancing separation region, the length of the separation region remaining substantially constant because the migration speeds of the front and rear boundaries are substantially identical;

supplying regenerating solutions to a regenerating region of the length of the ion exchange bed, whereby each portion of the length of the ion exchange bed may be repetitively used;

said solutions being supplied to maintain the speed of migration of the boundaries of the separation region at a controlled speed; and controlling the relative speed of movement between the length of the ion exchange bed and its surrounding chamber to be exactly equal to the migration speed of the boundaries, whereby the relative positions of the chamber and the boundaries is maintained stationary, and whereby the injection of solutions and withdrawal of solutions is constantly accurate notwithstanding such relative migration of boundaries along the length of the ion exchange bed and such relative movement between the ion exchange bed and its surrounding chamber.

3. The method of claim 2 in which a trivalent titanous region is maintained in advance of the front boundary of a uranium region and a ferric iron region is maintained at the rear of the rear boundary of a uranium region for separating uranium isotopes.

4. The method of claim 2 in which a vertical column of ion exchange bed is a stack of units which can be automatically pushed upwardly continuously while withdrawing units from an unloading zone and adding units to a loading zone, there being an air zone at the upper portion and an air zone at the lower portion of the column, said air zones protecting the loading zone and unloading zones from liquid flowing in the liquid flow zones of the vertical column.

5. The method of claim 2 in which the length of the ion exchange bed is a closed annulus, and in which a plurality of modifying zones are adapted to modify the flow of liquid around the circular path of the annulus.

6. The method of claim 4 in which a trivalent titanous region is maintained in advance of the front boundary of a uranium region and a ferric iron region is maintained at the rear of the rear boundary of a uranium region for separating uranium isotopes.

7. The method of claim 5 in which a trivalent titanous region is maintained in advance of the front boundary of a uranium region and a ferric iron region is maintained at the rear of the rear boundary of a uranium region for separating uranium isotopes.

* * * * *